(12) United States Patent
Peña et al.

(10) Patent No.: US 6,801,646 B1
(45) Date of Patent: Oct. 5, 2004

(54) SYSTEM AND METHOD FOR REDUCING OR ELIMINATING STREAK ARTIFACTS AND ILLUMINATION INHOMOGENEITY IN CT IMAGING

(75) Inventors: José Tamez Peña, Rochester, NY (US); Saara Marjatta Sofia Totterman, Rochester, NY (US); Kevin J. Parker, Rochester, NY (US)

(73) Assignee: VirtualScopics, LLC, Pittsford, NY (US)

( * ) Notice: Subject to any disclaimer, the term of this patent is extended or adjusted under 35 U.S.C. 154(b) by 260 days.

(21) Appl. No.: 09/908,492

(22) Filed: Jul. 19, 2001

(51) Int. Cl.[7] .............................. G06K 9/00; G06K 9/40; G01N 23/00
(52) U.S. Cl. .............................. 382/131; 382/274; 378/8
(58) Field of Search .............................. 382/131, 274, 382/261, 128; 378/4, 21–27, 8; 345/426

(56) References Cited

U.S. PATENT DOCUMENTS

| | | | | |
|---|---|---|---|---|
| 4,250,387 A | * | 2/1981 | Hounsfield et al. ............ 378/18 |
| 5,225,980 A | * | 7/1993 | Hsieh et al. ................... 378/18 |
| 5,305,204 A | * | 4/1994 | Ohhashi ....................... 382/131 |
| 5,561,695 A | | 10/1996 | Hu ................................ 378/8 |
| 5,774,521 A | * | 6/1998 | Close et al. ................... 378/62 |
| 5,818,231 A | * | 10/1998 | Smith .......................... 324/309 |
| 6,169,817 B1 | * | 1/2001 | Parker et al. ................ 382/131 |
| 6,246,783 B1 | * | 6/2001 | Avinash ....................... 382/128 |
| 6,370,224 B1 | * | 4/2002 | Simon et al. ................... 378/62 |
| 6,463,167 B1 | * | 10/2002 | Feldman et al. ............. 382/128 |
| 6,463,169 B1 | * | 10/2002 | Ino et al. ..................... 382/132 |
| 6,556,720 B1 | * | 4/2003 | Avinash ....................... 382/128 |

* cited by examiner

Primary Examiner—Mehrdad Dastouri
(74) Attorney, Agent, or Firm—Blank Rome LLP

(57) ABSTRACT

In CT (computed tomography) images, streak artifacts caused by the presence of metal implants and inhomogeneous estimation of tissue density are reduced or eliminated. The algorithm has two basic steps: 1) illumination correction and 2) adaptive 3D filtering. The algorithm starts by estimating the direction of the streak and the degree of inhomogeneous densities by gray scale morphology dilation. Then, it proceeds to estimate the correct densities based on the estimations and to reduce the streak by an adaptive 3D filtering whose parameters depend on the streak direction and the local image contrast.

12 Claims, 3 Drawing Sheets

SYSTEM AND METHOD FOR REDUCING OR ELIMINATING STREAK ARTIFACTS AND ILLUMINATION INHOMOGENEITY IN CT IMAGING

FIELD OF THE INVENTION

The present invention is directed to a system and method for processing images obtained through computed tomography (CT) or the like and more particularly to such a system and method in which artifacts caused by the presence of metal implants are reduced or eliminated.

DESCRIPTION OF RELATED ART

X-ray computed tomography (CT) is an important imaging technique, particularly in medical and dental applications. A series of X-ray beams from many different angles are used to create cross-sectional images of the patient's body. Those images from multiple slices are assembled in a computer into a three-dimensional picture that can display organs, bones, and tissues in great detail. CT offers high spatial resolution, three-dimensional registration and minimal blurring caused by motion.

However, the presence of strongly attenuating objects, such as metal implants or fillings, causes streak artifacts, also called starburst artifacts, in the image. Another problem encountered in CT is inhomogeneous estimation of tissue density caused by inhomogeneous illumination. While much investigation has been done into reducing or eliminating those problems, a satisfactory technique has not yet been found.

One attempt at a solution to the problem of artifacts caused by metal implants is found in U.S. Pat. No. 5,561,695 to Hu. The patent teaches a method for improving CT image quality in which data from a helical reconstruction are separated into a background component and a sharp-structure component. The separation can be performed using gray-scale thresholding, since the sharp structures and the image background usually have widely differing CT numbers. The image background is filtered to remove high-frequency artifacts. The images are recombined. However, the technique of Hu introduces more computational complexity than is desired, and the Hu approach does not appear to have been widely adopted by the radiology community.

SUMMARY OF THE INVENTION

It will be readily apparent from the above that a need exists in the art for a computationally efficient technique for reducing or eliminating streak artifacts and illumination inhomogeneity.

It is therefore an object of the present invention to reduce or eliminate streak artifacts caused by metal implants or the like.

It is another object of the present invention to correct illumination inhomogeneities.

It is still another object of the present invention to achieve the above objects in a computationally efficient way.

To achieve that and other objects, the present invention is directed to a technique for CT or other imaging that works directly with the reconstructed data. The technique has two basic steps: 1) illumination correction and 2) adaptive 3D filtering. The algorithm starts by estimating the direction of the streak and the degree of inhomogeneous densities by gray scale morphology dilation. Then, it proceeds to estimated the correct densities based on the estimations and to reduce the streak by an adaptive 3D filtering whose parameters depend on the streak direction and the local image contrast.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

The preferred embodiment of the present invention will now be set forth in detail with reference to the drawings.

Figure 1:
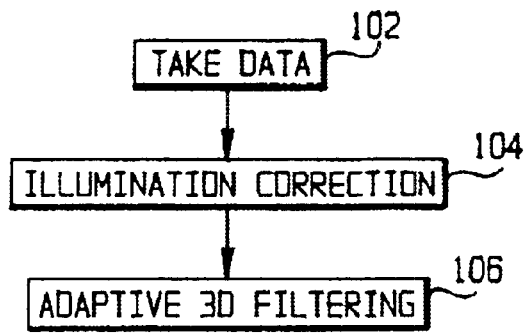
FIGS. 1–3 show flow charts of the process according to the preferred embodiment.

FIG. 1 shows an overview of the process carried out in the preferred embodiment. After the raw data have been taken in step 102, the process includes two steps: the illumination correction of step 104 and the adaptive 3D filtering of step 106. Those two steps will be explained in detail.

Figure 2:
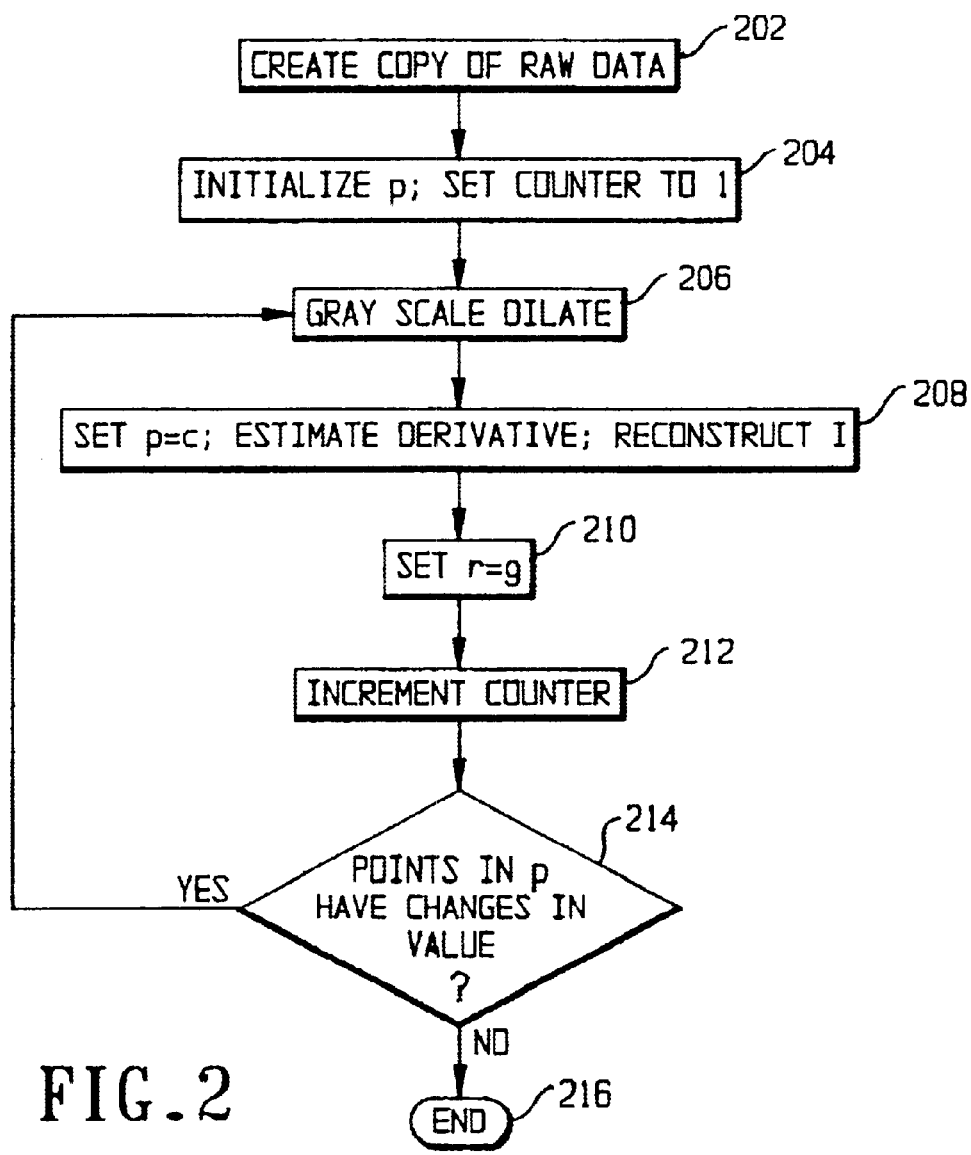

From a set of reconstructed CT images $f(x, y)$ that contain a metal implant, the algorithm proceeds to stack those images in a three dimensional (3D) volumetric image $f(x, y, z)$. Then, the algorithm gray scale dilates every single slice to estimate a propagation potential field $p(x, y, z)$ of the streak artifacts and to estimate the inhomogeneous illumination $I(x, y, z)$. The estimation of the potential field $p(x, y, z)$ via gray scale dilation is performed through the following steps shown in FIG. 2:

Step 202. Create a copy of the raw data: $r(x, y, z) = f(x, y, z)$

Step 204. Initiate $p(x, y, z) = 0$; set counter c to 1.

Step 206. Gray scale dilate every reconstructed CT slice image $f(x, y)$:

$$g(x,y) = r(x,y) \oplus h(x,y)$$

where $h(x, y)$ is the kernel $$h(x, y) = \begin{bmatrix} 0 & 1 & 0 \\ 1 & 1 & 1 \\ 0 & 1 & 0 \end{bmatrix}$$

for odd values of c and $$h(x, y) = \begin{bmatrix} 1 & 1 & 1 \\ 1 & 1 & 1 \\ 1 & 1 & 1 \end{bmatrix}$$

for even values of c. The dilation process establishes a growing front from the regions of high intensity.

Figure 3:
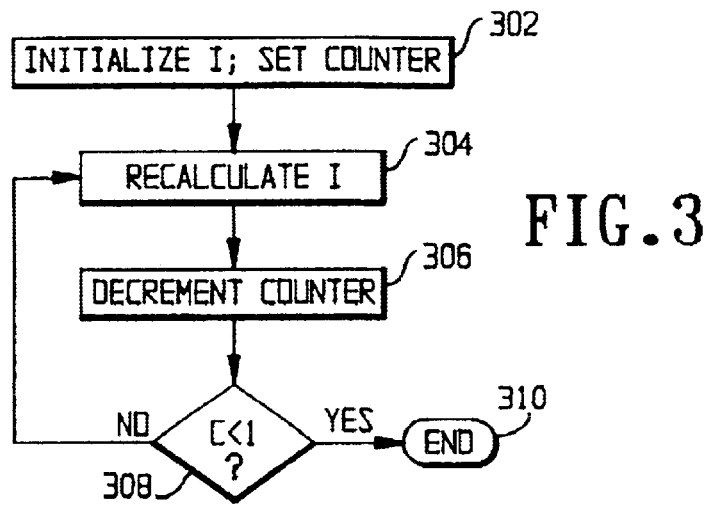

Step 208. Set $p(x, y, z) = c$ and estimate the derivative of the illumination function $I(x, y, z)$ along the growing path for all the points where $g(x, y, z) > r(x, y, z)$. From the directional derivative, reconstruct the illumination function. That step will be described below with reference to FIG. 3.

Step 210. Set $r(x, y, z) = g(x, y, z)$.

Step 212. Increment c: $c = c+1$.

Step 214. Determine whether any points in p(x, y, z) have changes in value. If so, steps 206–212 are repeated. Otherwise, the process ends in step 216.

The reconstruction of the illumination function, mentioned above with reference to step 208, will now be described. The metal inside the body will introduce some changes in the illumination profile of the image. It is assumed that the image is composed of piece-wise elements, each one with uniform density. Therefore, there should not be any strong variations on the image density inside any tissue, and the illumination function can be reconstructed by integrating the estimation of the illumination derivative, $$\frac{\partial}{\partial c} I(x, y, z),$$

in the direction of the propagation front. The estimation of $$\frac{\partial}{\partial c} I(x, y, z)$$

is done by an adaptive weighted difference of the neighborhood differences and the previous neighborhood estimations of $$\frac{\partial}{\partial c} I(x, y, z).$$

I(x, y, z).
If $$\frac{\partial}{\partial c} I(x, y, z)$$

is initialized to zero in step 202 of the propagation front estimation, then in step 208, the directional derivtive is estimated using the following formulation:

$$\frac{\partial}{\partial c} I(x, y, z) =$$

$$u \sum_{i=-1}^{1} \sum_{j=-1}^{1} (\omega(i, j, c)[(1.0 - \gamma(i, j))(f(x+i, y+j, z) - f(x, y, z)) +$$

$$\gamma(i, j) I_p(x+i, y+j, z)])$$

where $$\omega(i, j, c) = e^{(ac)^2} \left( \begin{cases} 1 & \text{if } g(x+i, y+j, z) > r(x+i, y+j, z) \\ 0 & \text{otherwise} \end{cases} \right),$$

u is a normalization constant such that $ue^{(ac)_2} \Sigma\Sigma\omega(i, j, c)=1$, and $$\gamma(i, j) = \begin{cases} 1 & \text{if } \left| \log\left[ |f(x+i, y+j, z) - f(x, y, z)| / \frac{\partial}{\partial c} I(x+i, y+j, z) \right] \right| < \sigma \\ 0 & \text{otherwise} \end{cases}.$$

The above equations provide an estimation of the illumination directional derivative at all points where p(x, y, z)=c.

The quantity σ is the discontinuity threshold and depends on the body being imaged. For human studies, a good threshold is σ=0.14. On the other hand, the constant α depends on the image resolution. For a voxel resolution of 0.5×0.5 mm², a good value is α=0.03. It will be seen from the above that the weighting function ω(i, j, c) depends on the growing front, while γ(i, j) depends on the image discontinuities.

Once the derivative of the illumination function has been estimated, it is integrated to get the illumination function. The integration starts by setting I(x, y, z)=k, where k is a constant equal to the mean image intensity. Once I(x, y, z) has been initialized, the integration starts from the outer boundary of the image to the point where the potential image is zero. The process is carried out through the following steps shown in FIG. 3:

Step 302. Initialize I(x, y, z)=k; set counter c to the maximum potential, c=max(p(x, y, z)).

Step 304. Look at the neighborhood of all the points where p(x, y, z)=c; at those points, $$I(x, y, z) = u \sum_{i=-1}^{1} \sum_{j=-1}^{1} \left( \beta(i, j) \left[ \frac{\partial}{\partial c} I(x+i, y+j, z) + I(x, y, z) \right] \right),$$

where $$\beta(i, j) = \begin{cases} 1 & \text{if } p(x+i, y+j, z) > p(x, y, z) \\ 0 & \text{otherwise} \end{cases}$$

and u is a normalization constant such that $u\Sigma\Sigma\beta(i, j)=1$.

Step 306. Decrement c: c=c−1.

Step 308. Determine whether c<1. Repeat steps 304 and 306 until c<1, at which time the process ends in step 310.

Once the illumination field is found, the illumination inhomogeneity in f(x, y, z) is corrected:

$$g(x, y, z) = \frac{f(x, y, z)k}{I(x, y, z)}.$$

The new coverage image g(x, y, z) has smaller variations in the image intensity than the original image, particularly at those points at which the density should be constant.

In the real world the original image has been degraded in such a way that the discontinuity detection can be very hard. To avoid that problem, the image f(x, y, z) is pre-filtered with a non-linear structure preserving filter that reduced the noise around some of the streak artifacts. The filtered image was used for the estimation of the illumination profile.

Once the image has been corrected as described above, the streak artifact can be reduced. A 3×3×3 adaptive filter L(x, y, z) is used to reduce the streak artifact. The filter coefficient is a function if the propagation potential and the local image contrast and is given by $$L(x, y, z) = \frac{(s\eta)}{(s + (0.1 + (p(x_0 + x, y_0 + y, z_0 + z) - p(x_0, y_0, z_0))^2)(g(x_0 + x, y_0 + y, z_0 + z) - g(x_0, y_0, z_0))^2)}$$

where s is the noise estimation variance at point $(x_0, y_0, z_0)$ and η is the normalization constant.

Coefficients at neighboring points with different potential as well as those neighboring points whose density is very different will be very small. On the other hand, coefficients at neighboring points with similar potential and very similar density compared to the noise estimation variance are larger. This formulation reduces artifacts and preserves points where is a strong contrast between tissues.

The final processed image $h(x_0, y_0, z_0)$ at the point $(x_0, y_0, z_0)$ is given by $$h(x_0, y_0, z_0) = \sum_{x=-1}^{1}\sum_{y=-1}^{1}\sum_{z=-1}^{1} L(x_0+x, y_0+y, z_0+z)g(x_0+x, y_0+y, z_0+z).$$

The adaptive filtering process can be done several times so that it effectively removes most of the streaks present in the image.

In cases where the in-plane resolution is much finer than the slice thickness, the adaptive filter can be modified in such a way as to avoid degrading the image. The image quality can also be improved by providing a space and streak oriented noise estimation. If that way, those regions are filtered where the streak artifacts are more important, and filtering can be avoided in those regions where the streaks are not so strong.

Figures 5A, 5B:
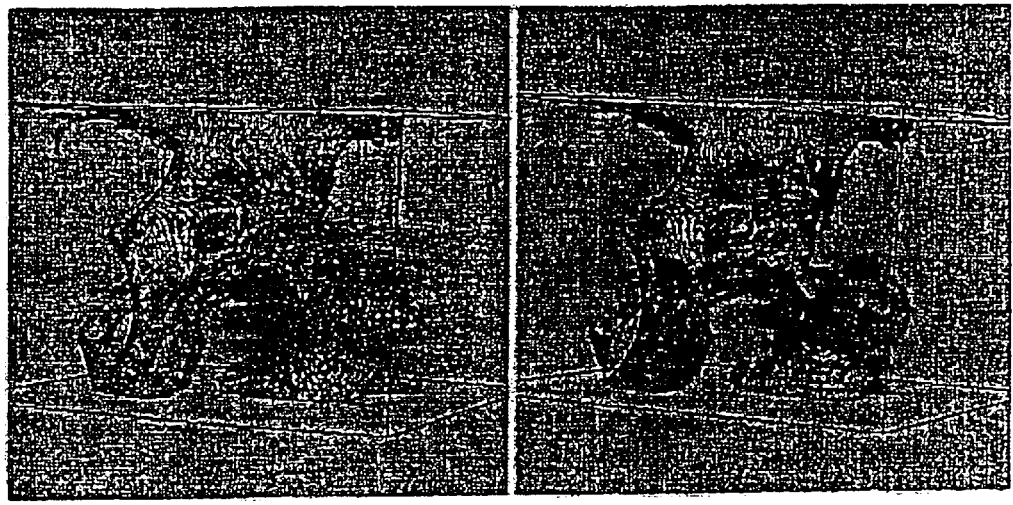
FIGS. 5A and 5B show volume renderings of the image from raw data and processed data, respectively.
Figure 4A:
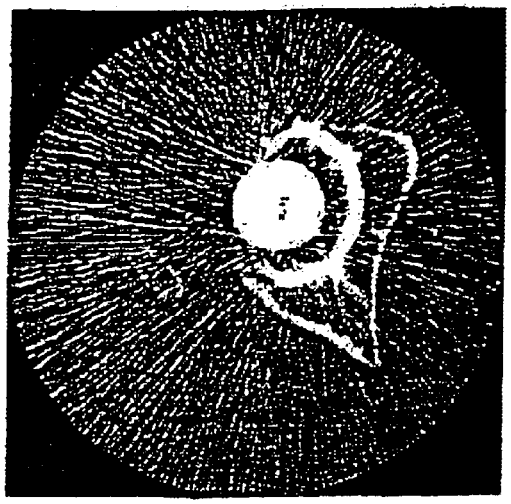
FIGS. 4A–4E show steps in the processing of a slice of an image.
Figure 4B:
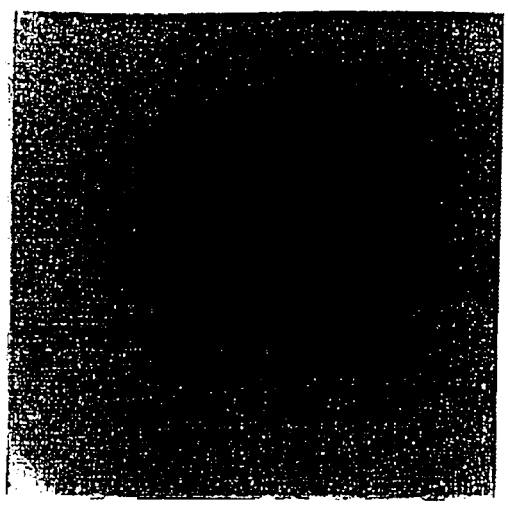
Figure 4C:
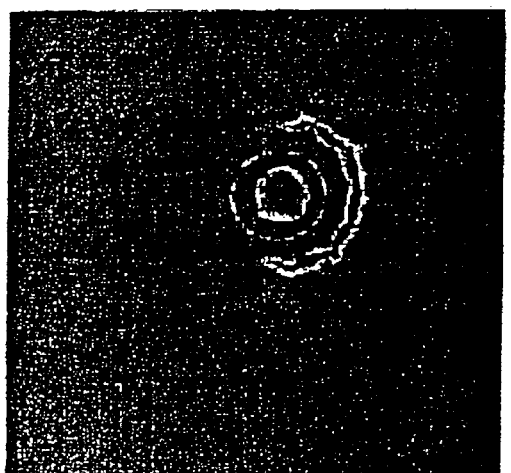
Figure 4D:
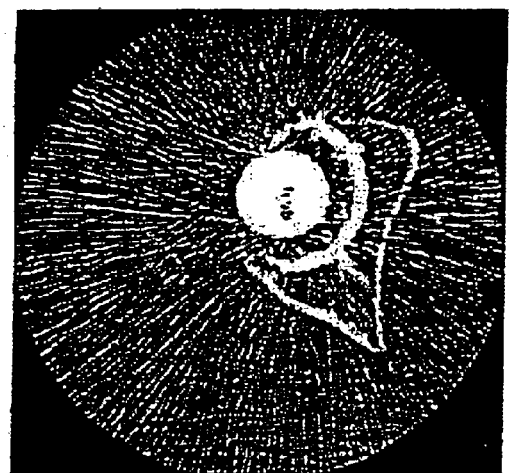
Figure 4E:
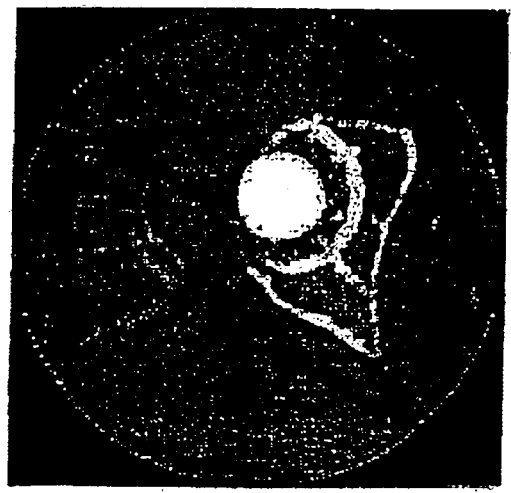

The algorithm has been tested on several CT images with a hip prosthesis. FIG. 4A shows a single slice of one of those images. The images slice contains the femur stem and the prosthesis cup. FIG. 4B shows the estimated potential field, while FIG. 4C shows the estimation of the illumination field. FIG. 4D is the CT image after removing the illumination artifacts. FIG. 4E shows the filtered image after smoothing the artifacts with the adaptive filter. FIGS. 5A and 5B show the volume rendering of the hip from the raw data and the processed data, respectively. As one can see the volumetric rendering of the hip from the processed data allows to see the metal prosthesis as well as more detail in the bone that surrounds the prosthesis.

Figure 6:
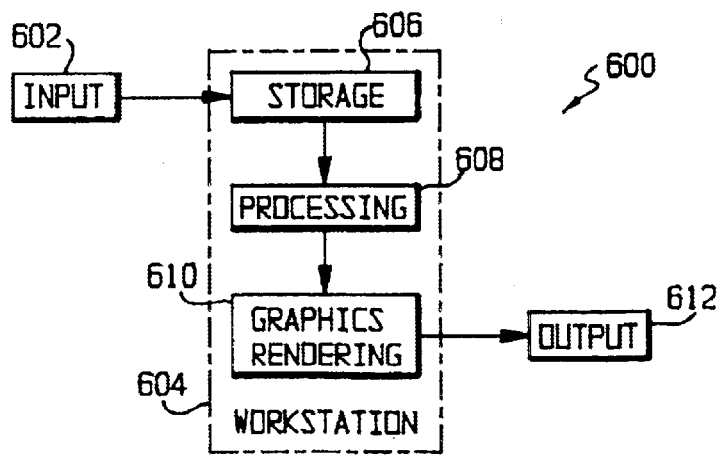
FIG. 6 shows a block diagram of a system on which the preferred embodiment can be implemented.

The embodiment disclosed above and other embodiments can be implemented in a system such as that shown in the block diagram of FIG. 6. The system 600 includes an input device 602 for input of the image data and the like. The information input through the input device 602 is received in the workstation 604, which has a storage device 606 such as a hard drive, a processing unit 608 for performing the processing disclosed above, and a graphics rendering engine 610 for preparing the final processed image for viewing, e.g., by surface rendering. An output device 612 can include a monitor for viewing the images rendered by the rendering engine 610, a further storage device such as a video recorder for recording the images, or both. Illustrative examples of the workstation 604 and the graphics rendering engine 610 are a Silicon Graphics Indigo workstation and an Irix Explorer 3D graphics engine.

While a preferred embodiment has been set forth above detail, those skilled in the art who have reviewed the present disclosure will readily appreciate that other embodiments can be realized within the scope of the invention. For example, numerical values, such as those given for $\alpha$ and $\sigma$, are illustrative rather than limiting. Also, the imaged object can be any human or animal body part or any other object. Moreover, the invention has applicability to imaging technologies other than CT. Therefore, the present invention should be construed as limited only by the appended claims.

We claim:

1. A method for imaging an object while reducing artifacts and improving a uniformity of illumination in the image, the method comprising:
   (a) receiving raw imaging data from the object;
   (b) estimating an illumination function from the raw imaging data;
   (c) correcting the raw imaging data in accordance with the estimated illumination function to obtain an illumination corrected image;
   (d) preparing an adaptive filter from the illumination corrected image; and
   (e) preparing a final processed image from the adaptive filter and the illumination corrected image;
   wherein the step of estimating the illumination function comprises:
      (i) creating a copy of the raw imaging data;
      (ii) initializing a potential field to zero;
      (iii) initializing a first counter to one;
      (iv) gray scale dilating the raw imaging data in accordance with a value of the counter to obtain gray scale dilated data;
      (v) setting the potential field equal to the first counter;
      (vi) estimating a directional derivative of the illumination function;
      (vii) reconstructing the illumination function from the directional derivative;
      (viii) setting the raw imaging data equal to the gray scale dilated data;
      (ix) incrementing the first counter; and
      (x) repeating steps (iv) through (ix) until no points in the potential field have changes in value.

2. The method of claim 1, wherein the directional derivative at each point is estimated from the raw imaging data at that point and the raw imaging data at adjacent points.

3. The method of claim 2, wherein the illumination function is reconstructed. by:
   (A) initializing the illumination function to a constant equal to a mean image intensity;
   (B) initializing the second counter to a maximum value of the potential field;
   (C) recalculating the intensity function from the intensity function and the directional derivative of the intensity function;
   (D) decrementing the second counter; and
   (E) repeating steps (C) and (D) until the second counter is below a threshold counter value.

4. The method of claim 3 wherein the threshold counter value is one.

5. The method of claim 1 wherein the adaptive filter at each point is a function of the potential field and the illumination corrected image.

6. The method of claim 5 wherein the final processed image at each point is a function of the adaptive filter and the illumination corrected image at that point and at adjacent points.

7. A system for imaging an object while reducing artifacts and improving a uniformity of illumination in the image, the system comprising:
   an input for receiving raw imaging data;
   a processor for estimating an illumination function from the raw imaging data, correcting the raw imaging data in accordance with the estimated illumination function to obtain an illumination corrected image, preparing an adaptive filter from the illumination corrected image, and preparing a final processed image from the adaptive filter and the illumination corrected image; and
   an output for outputting the final processed image;
   wherein the processor estimates the illumination function by:
      (i) creating a copy of the raw imaging data;
      (ii) initializing a potential field to zero;
      (iii) initializing a first counter to one;
      (iv) gray scale dilating the raw imaging data in accordance with a value of the counter to obtain gray scale dilated data;

(v) setting the potential field equal to the first counter;
(vi) estimating a directional derivative of the illumination function;
(vii) reconstructing the illumination function from the directional derivative;
(viii) setting the raw imaging data equal to the gray scale dilated data;
(ix) incrementing the first counter; and
(x) repeating steps (iv) through (ix) until no points in the potential field have changes in value.

8. The system of claim 7, wherein the directional derivative at each point is estimated from the raw imaging data at that point and the raw imaging data at adjacent points.

9. The system of claim 8, wherein the illumination function is reconstructed by:
(A) initializing the illumination function to a constant equal to mean image intensity;
(B) initializing a second counter to a maximum value of the potential field;
(C) recalculating the intensity function from the intensity function and the directional derivative of the intensity function;
(D) decrementing the second counter; and
(E) repeating steps (C) and (D) until the second counter is below a threshold counter value.

10. The system of claim 9, wherein the threshold counter value is one.

11. The system of claim 7, wherein the adaptive filter at each point is a function of the potential field and the illumination corrected image.

12. The system of claim 11, wherein the final processed image at each point is a function of the adaptive filter and the illumination corrected image at that point and at adjacent points.

* * * * *